US00PP14645P29

(12) United States Plant Patent
Strope

(10) Patent No.: US PP14,645 P2
(45) Date of Patent: Mar. 30, 2004

(54) NEW GUINEA IMPATIENS PLANT NAMED 'BALCELPINK'

(50) Latin Name: *Impatiens hawkeri*
Varietal Denomination: Balcelpink

(75) Inventor: Kerry M. Strope, Jefferson City, MO (US)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/359,750

(22) Filed: Feb. 6, 2003

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—June Hwu
(74) *Attorney, Agent, or Firm*—C. A. Whealy

(57) ABSTRACT

A new and distinct cultivar of New Guinea Impatiens plant named 'Balcelpink', characterized by its upright, uniform and mounded plant habit; large dark pink-colored flowers that are positioned above and beyond the leaves; and green-colored leaves.

1 Drawing Sheet

Botanical classification/cultivar denomination: *Impatiens hawkeri* cultivar Balcelpink.

BACKGROUND OF THE INVENTION

The present Invention relates to a new and distinct cultivar of New Guinea Impatiens plant, botanically known as *Impatiens hawkeri*, and hereinafter referred to by the name 'Balcelpink'.

The new Impatiens is a product of a planned breeding program conducted by the Inventor in Arroyo Grande, Calif. The objective of the breeding program is to develop New Guinea Impatiens cultivars that have a freely basal branching growth habit and numerous large flowers with attractive flower colors.

The new Impatiens originated from a cross-pollination made by the Inventor in 2000 of the *Impatiens hawkeri* cultivar Moorea, disclosed in U.S. Plant Pat. No 9,147, as the female, or seed parent, with a proprietary selection of *Impatiens hawkeri* identified as code number 1508, not patented, as the male, or pollen parent. The cultivar Balcelpink was discovered and selected by the Inventor as a flowering plant within the progeny of the stated cross-pollination in a controlled environment in Arroyo Grande, Calif.

Asexual reproduction of the new cultivar by terminal cuttings taken in Arroyo Grande, Calif. since March, 2000 has shown that the unique features of this new Impatiens are stable and reproduced true to type in successive generations.

SUMMARY OF THE INVENTION

The following traits have been repeatedly observed and are determined to be the unique characteristics of 'Balcelpink'. These characteristics in combination distinguish 'Balcelpink' as a new and distinct New Guinea Impatiens cultivar:

1. Upright, uniform and mounded plant habit.
2. Large dark pink-colored flowers that are positioned above and beyond the leaves.
3. Green-colored leaves.

Plants of the new Impatiens differ primarily from plants of the female and male parents in flower and leaf coloration.

Plants of the new Impatiens can be compared to plants of the cultivar Fisnics Pink, disclosed in U.S. Plant Pat. No. 13,228. In side-by-side comparisons conducted in West Chicago, Ill., plants of the new Impatiens differed from plants of the cultivar Fisnics Pink in the following characteristics:

1. Plants of the new Impatiens had shorter lateral branches with shorter internodes than plants of the cultivar Fisnics Pink.
2. Plants of the new Impatiens had longer leaves than plants of the cultivar Fisnics Pink.
3. Plants of the new Impatiens had larger flowers than plants of the cultivar Fisnics Pink.
4. Plants of the new Impatiens had shorter peduncles than plants of the cultivar Fisnics Pink.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Impatiens.

The photograph at the top of the sheet comprises a side perspective view of a typical flowering plant of 'Balcelpink' grown in a container.

The photograph at the bottom of the sheet is a close-up view of typical flowers of 'Balcelpink'.

DETAILED BOTANICAL DESCRIPTION

The cultivar Balcelpink has not been observed under all possible environmental conditions. The phenotype may vary somewhat with variations in environment such as temperature and light intensity without, however, any variance in genotype.

The aforementioned photographs and following observations and measurements describe plants grown in West Chicago, Ill., under commercial practice in a polycarbonate-covered greenhouse with day temperatures ranging from 20 to 24° C., night temperatures ranging from 14 to 18° C. and light levels ranging from 4,000 to 7,000 footcandles. Rooted young plants were planted in 10-cm containers and had been growing for about 13 weeks when the photographs and the description were taken.

In the following description, color references are made to The Royal Horticultural Society Colour Chart, 2001 Edition, except where general terms of ordinary dictionary significance are used.

Botanical classification: *Impatiens hawkeri* cultivar Balcelpink.

Parentage:

*Female parent.*—*Impatiens hawkeri* cultivar Moorea, disclosed in U.S. Plant Pat. No. 9,147.

*Male parent.*—Proprietary selection of *Impatiens hawkeri* identified as code number 1508, not patented.

Propagation:

*Type cutting.*—Terminal cuttings.

*Time to initiate roots.*—About 7 days at 18° C.

*Time to produce a rooted cutting.*—About 21 days at 18° C.

*Root description.*—Fine, fibrous and white in color.

*Rooting habit.*—Freely branching.

Plant description:

*General appearance.*—Upright, uniform and mounded plant habit; freely basal branching growth habit, about four basal branches develop per plant. Moderately vigorous.

*Plant height.*—About 17.3 cm.

*Plant diameter or spread.*—About 31.8 cm.

*Lateral branches.*—Length: About 8.3 cm. Diameter: About 9 mm. Internode length: About 2.4 cm. Color: 144B.

*Foliage description.*—Arrangement: Opposite or in whorls of three to five. Length: About 9.6 cm. Width: About 3.4 cm. Shape: Elliptic. Apex: Acuminate. Base: Attenuate. Margin: Serrulate with ciliation. Texture, upper and lower surfaces: Smooth, glabrous. Venation pattern: Pinnate. Color: Young foliage, upper surface: 146A. Young foliage, lower surface: 147B. Fully expanded foliage, upper surface: 137A. Fully expanded foliage, lower surface: 147B. Venation, upper surface: Midvein, 145C occasionally overlain with 63B; lateral veins, 145C. Venation, lower surface: 145C. Petiole: Length: About 1.5 cm. Diameter: About 3.3 mm. Texture, upper and lower surfaces: Smooth, glabrous. Color, upper and lower surfaces: 145C.

Flower description:

*Flower type and flowering habit.*—Single large flowers. Freely flowering, usually about three flowers and flower buds per lateral branch. Flowers positioned above and beyond the foliage and typically face upward or outward. Flowers not fragrant. Petals self-cleaning; gynoecium persistent.

*Flower longevity.*—Flowers last about one week on the plant.

*Flowering season.*—Year-round under greenhouse conditions; in the garden, flowering from spring until fall, flowering continuous.

*Flower buds.*—Length: About 2.2 cm. Diameter: About 1.4 cm. Shape: Ovoid. Color: N66B.

*Flower diameter.*—About 7.5 cm.

*Flower depth.*—About 1.8 cm.

*Flower shape.*—Rounded.

*Petals.*—Quantity: Five per flower, imbricate. Length, banner petal: About 3.6 cm. Length, lateral petals: About 3.7 cm. Length, basal petals: About 3.9 cm. Width, banner petals: About 5.7 cm. Width, lateral petals: About 4.5 cm. Width, basal petals: About 5.4 cm. Shape: Obovate. Apex: Emarginate. Base, banner petal: Truncate. Base, lateral and basal petals: Attenuate. Margin: Entire. Texture, upper and lower surfaces: Smooth, glabrous. Color: When opening, upper surface: 73A. When opening, lower surface: 73B. Fully opened, upper surface: N66C; towards base, N66A. Fully opened, lower surface: 68B. Spur: Quantity: One per flower. Length: About 7.5 cm. Aspect: Slightly curved. Color: 53C; towards apex, 144C.

*Peduncles.*—Length: About 6 cm. Diameter: About 1 mm. Strength: Strong; flexible. Angle: Acute. Color: 145A overlain with 53B.

*Reproductive organs.*—Androecium: Stamen quantity/arrangement: Five fused at anthers, hooded; filaments free. Anther length: About 1 mm. Anther shape: Obovate. Anther color: 56D. Pollen amount: Moderate. Pollen color: 11D. Gynoecium: Pistil quantity: One per flower. Pistil length: About 6 mm. Stigma length: Less than 1 mm. Stigma color: Colorless. Style length: Less than 1 mm. Style color: 50B. Ovary arrangement: Five-celled. Ovary length: About 1 mm. Ovary texture: Smooth. Ovary color: N144C.

*Seeds/fruits.*—Seed and fruit development has not been observed.

Disease/pest resistance: Plants of the new Impatiens have not been observed to be resistant to pathogens and pests common to New Guinea Impatiens.

It is claimed:

1. A new and distinct cultivar of New Guinea Impatiens plant named 'Balcelpink', as illustrated and described.

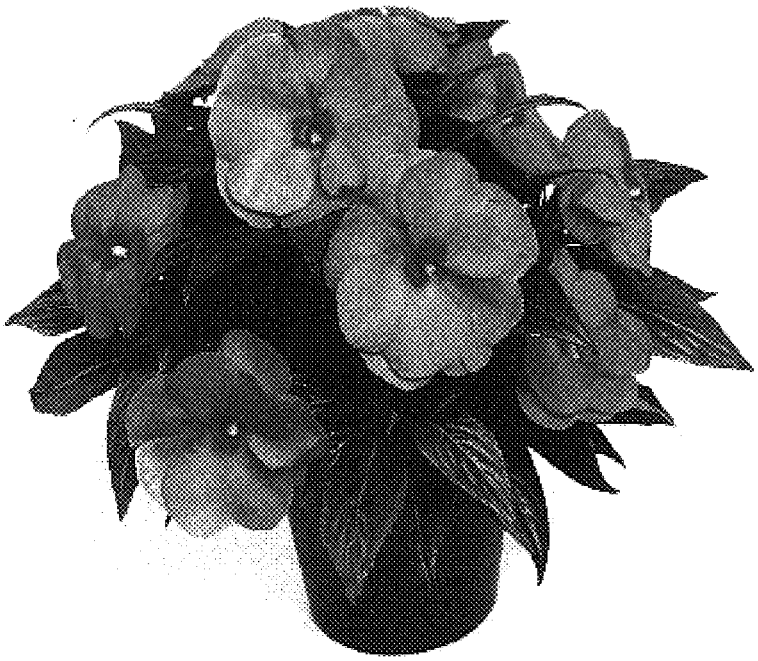
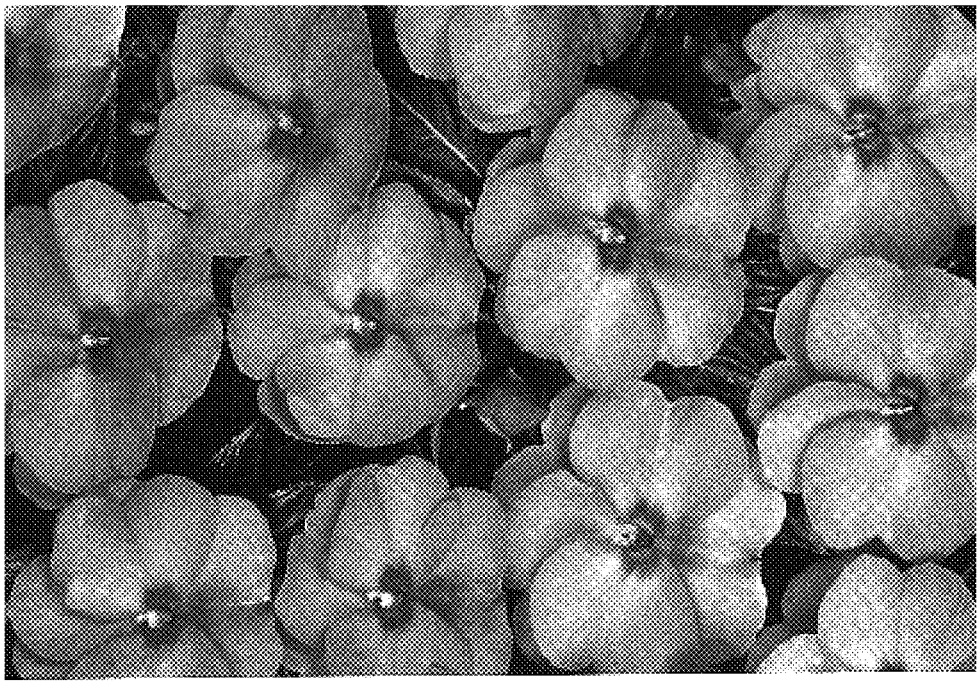

* * * * *